United States Patent
Gerard et al.

(10) Patent No.: US 11,619,381 B2
(45) Date of Patent: Apr. 4, 2023

(54) CATALYTIC COMBUSTION BURNER MADE OF POROUS MATERIAL, WITH OPTIMISED OPERATING PERFORMANCE AND BOTTLE EQUIPPED WITH SUCH A BURNER

(71) Applicant: PRODUITS BERGER, Grand Bourgtheroulde (FR)

(72) Inventors: Corinne Gerard, Incarville (FR); Laurent Ozouf, Notre Dame de Bliquetuit (FR); Laetitia Pajot, Condat sur Vienne (FR); Matthieu Cellier, Saint Jouvent (FR)

(73) Assignee: Produits Berger, Grand Bourgtheroulde (FR)

( * ) Notice: Subject to any disclaimer, the term of this patent is extended or adjusted under 35 U.S.C. 154(b) by 444 days.

(21) Appl. No.: 16/474,332

(22) PCT Filed: Dec. 21, 2017

(86) PCT No.: PCT/FR2017/053761
§ 371 (c)(1),
(2) Date: Jun. 27, 2019

(87) PCT Pub. No.: WO2018/122502
PCT Pub. Date: Jul. 5, 2018

(65) Prior Publication Data
US 2019/0338946 A1    Nov. 7, 2019

(30) Foreign Application Priority Data
Dec. 30, 2016  (FR) ........................... 1663555

(51) Int. Cl.
*F23D 3/18*        (2006.01)
*A61L 9/03*        (2006.01)

(52) U.S. Cl.
CPC ............... *F23D 3/18* (2013.01); *A61L 9/037* (2013.01); *F23D 2900/03081* (2013.01); *F23D 2900/05002* (2013.01)

(58) Field of Classification Search
CPC ..... F23D 3/18; F23D 3/40; F23D 3/26; F23D 2900/03081; F23D 2900/05002;
(Continued)

(56) References Cited

U.S. PATENT DOCUMENTS

| | | | | |
|---|---|---|---|---|
| 2,997,869 A | * | 8/1961 | Weiss ...................... | D06F 75/02 431/147 |
| 3,343,586 A | * | 9/1967 | Berchtold ............... | F23D 91/02 431/241 |

(Continued)

FOREIGN PATENT DOCUMENTS

| | | | | |
|---|---|---|---|---|
| DE | 2938523 A1 | * | 9/1980 | ............. H01M 4/90 |
| EP | 0277875 A1 | * | 8/1988 | ............... F23D 3/08 |

(Continued)

OTHER PUBLICATIONS

"EP_1491819_A1_M—Machine Translation.pdf", machine translation, EPO.org. (Year: 2021).*
(Continued)

*Primary Examiner* — Steven B Mcallister
*Assistant Examiner* — Daniel E. Namay
(74) *Attorney, Agent, or Firm* — Patterson Thuente, P.A.

(57) ABSTRACT

A catalytic combustion burner made of porous material and a bottle equipped with such a burner have an optimized operating performance, which enables the burner to withstand and not be extinguished when it is subjected to strong air currents such as air conditioning.

14 Claims, 10 Drawing Sheets

(58) Field of Classification Search
CPC ........... F23D 2900/00001; F23D 5/126; F23D 2209/20; F23D 2206/0063; F23D 2202/00; A61L 19/037; A61L 19/03; F23C 13/08; F23C 2900/13002; F24V 30/00
USPC .................................. 431/268; 126/401–414
See application file for complete search history.

(56) References Cited

U.S. PATENT DOCUMENTS

| | | | | |
|---|---|---|---|---|
| RE26,976 E | * | 10/1970 | Berchtold et al. | F23D 91/02 431/241 |
| 4,235,748 A | * | 11/1980 | Berchielli | H01M 4/90 502/151 |
| 4,368,029 A | * | 1/1983 | Lacroix | B01J 23/34 431/328 |
| 4,476,011 A | * | 10/1984 | Tait | B01J 29/061 208/110 |
| 4,618,594 A | * | 10/1986 | Tait | B01J 29/061 502/204 |
| 4,738,768 A | * | 4/1988 | Tait | B01J 29/061 208/111.3 |
| 4,981,576 A | * | 1/1991 | Tait | B01J 23/8878 208/111.15 |
| 5,169,300 A | * | 12/1992 | Chou | B01J 23/63 423/453 |
| 5,173,174 A | * | 12/1992 | Upson | B01J 29/084 208/113 |
| 5,378,142 A | * | 1/1995 | Kennelly | B01J 23/63 431/7 |
| 5,840,246 A | * | 11/1998 | Hammons | A61L 9/03 239/54 |
| 6,015,287 A | * | 1/2000 | Berlaimont | F23C 13/08 431/339 |
| 6,451,841 B2 | * | 9/2002 | Lehoux | A01N 25/20 514/421 |
| 6,537,061 B1 | * | 3/2003 | Gomez | A01M 1/2088 431/268 |
| 6,579,090 B1 | * | 6/2003 | Taubitz | F23D 3/24 431/126 |
| 6,814,929 B2 | * | 11/2004 | Lehoux | A01N 31/08 422/4 |
| 7,137,811 B2 | * | 11/2006 | Lehoux | A61L 9/037 431/268 |
| 7,241,136 B2 | * | 7/2007 | Lehoux | F23D 3/02 431/324 |
| 8,062,389 B2 | * | 11/2011 | Pisklak | C10L 1/1802 44/388 |
| 9,146,036 B2 | * | 9/2015 | Tang | A61L 9/037 |
| 9,203,155 B2 | * | 12/2015 | Choi | B82Y 20/00 |
| 9,279,583 B2 | * | 3/2016 | Pisklak | F23D 3/40 |
| 9,974,879 B2 | * | 5/2018 | Nettleton | B01J 23/10 |
| 10,112,181 B2 | * | 10/2018 | Katoh | B01J 35/108 |
| 10,323,554 B2 | * | 6/2019 | Suzuki | B01J 35/108 |
| 2004/0265762 A1 | * | 12/2004 | Lehoux | A61L 9/037 431/268 |
| 2005/0037309 A1 | * | 2/2005 | Lehoux | F23D 3/02 431/326 |
| 2005/0074370 A1 | * | 4/2005 | Yuan | A61L 9/037 422/126 |
| 2005/0147540 A1 | * | 7/2005 | Huang | A61L 9/037 422/125 |
| 2007/0134607 A1 | * | 6/2007 | Chen | F23D 3/40 431/299 |
| 2007/0202450 A1 | * | 8/2007 | Pisklak | F23D 3/24 431/320 |
| 2008/0014539 A1 | * | 1/2008 | Pisklak | C10L 1/305 431/268 |
| 2008/0090188 A1 | * | 4/2008 | Pisklak | F23D 5/126 431/7 |
| 2010/0215549 A1 | * | 8/2010 | Corda | F23D 3/18 422/122 |
| 2012/0245024 A1 | * | 9/2012 | Chaput | C04B 33/04 502/339 |
| 2014/0272744 A1 | * | 9/2014 | Tang | A61L 9/037 431/328 |
| 2015/0151018 A1 | * | 6/2015 | Nettleton | F23D 3/40 431/323 |
| 2017/0074508 A1 | * | 3/2017 | Pisklak | F23D 3/24 |
| 2018/0236847 A1 | * | 8/2018 | Moesl | F23D 3/40 |

FOREIGN PATENT DOCUMENTS

| | | | | |
|---|---|---|---|---|
| EP | 0785395 A2 | * | 7/1997 | ............ F23D 5/126 |
| EP | 1491818 A1 | * | 12/2004 | ............ F23D 3/02 |
| EP | 1491819 | | 12/2004 | |
| EP | 1491819 A1 | * | 12/2004 | ......... A01M 1/2088 |
| FR | 2162772 A5 | * | 7/1973 | ............ F23D 91/02 |
| FR | 2450121 A1 | * | 9/1980 | ............ H01M 4/90 |
| FR | 2483782 A1 | * | 12/1981 | ............ F23D 99/00 |
| FR | 2530144 A1 | * | 1/1984 | ............ A61L 9/03 |
| FR | 2610390 | | 8/1988 | |
| FR | 2779509 | | 12/1999 | |
| FR | 2905163 | | 2/2008 | |
| FR | 2905164 | | 2/2008 | |
| FR | 2905165 | | 2/2008 | |
| GB | 1001901 A | * | 8/1965 | ............ B22D 7/104 |
| JP | 2001324109 A | * | 11/2001 | ............ F23D 3/02 |
| JP | 2002047114 A | * | 2/2002 | ............ A01N 25/20 |
| JP | 2003190268 A | * | 7/2003 | ............ A61L 9/12 |
| JP | 2005016925 A | * | 1/2005 | ............ F23C 13/00 |
| JP | 2005016926 A | * | 1/2005 | ............ F23D 3/24 |
| TW | 201215417 | | 4/2013 | |
| WO | WO-2008023111 A1 | * | 2/2008 | ............ F23D 3/40 |
| WO | WO-2010133565 A1 | * | 11/2010 | ......... B01J 35/0026 |

OTHER PUBLICATIONS

"FR_2610390_B1_M—Machine Translation.pdf", machine translation, EPO.org. (Year: 2021).*
"WO_2008023111_A1_M—Machine Translation.pdf", machine translation, EPO.org. (Year: 2021).*
International Search Report (English translation) and Written Opinion for PCT/FR2017/053761 dated Apr. 9, 2018.

* cited by examiner

CATALYTIC COMBUSTION BURNER MADE OF POROUS MATERIAL, WITH OPTIMISED OPERATING PERFORMANCE AND BOTTLE EQUIPPED WITH SUCH A BURNER

RELATED APPLICATIONS

This present application is a National Phase entry of PCT Application No. PCT/FR2017/053761 filed Dec. 21, 2017, which claims priority to French Application No. 1663555 filed Dec. 30, 2016, the contents of each being incorporated herein by reference in their entireties.

TECHNICAL FIELD

Embodiments of the present invention relate generally to the field of catalytic combustion, and more precisely to that of catalytic combustion burners made of porous material. These burners are used in particular for diffusing fragrance and/or active substances, for destroying molecules which may or may not be odorous, and/or for purifying the air.

BACKGROUND ART

Such a burner was described, for example, in patent FR 2610390 in the name of the Applicant. It is especially intended to receive a wick dipping in a combustible liquid contained in a catalytic combustion bottle, which receives the burner on its neck. Such a burner (represented especially in FIG. 1) is made of a porous material, which comprises an end piece having, in its upper part, a cavity emerging to the exterior and, in its lower part, a cavity in which the end of the wick is engaged. The end piece is extended in its lower part by a sleeve. When functioning, the combustible liquid conveyed by the wick penetrates the pores of the porous material of the burner. Some of this liquid crosses the central zone of the burner and undergoes vaporization therein.

Moreover, the Applicant has developed an SiC-based ceramic burner such as, for example, those described in French patents FR2905163B1, FR2905164B1 and FR2905165B1 belonging to the Applicant, to equip catalytic lamps. This type of burner meets numerous performance criteria in terms of fragrancing, consumption, olfactory quality, emissions, etc. However, it has the drawback of malfunctioning or even of going out when it is subjected to strong air currents such as air conditioning. Certain countries, in which air conditioning is extensively used, are thus confronted with recurring problems of burner extinction when the lamp is placed close to air conditioning, and therefore cannot use the burners mentioned previously.

SUMMARY OF THE INVENTION

In order to overcome the abovementioned drawbacks, the Applicant has developed a catalytic combustion burner made of porous material, comprising:
an end piece comprising:
a lower part of outside diameter $\phi_1$ and delimiting a first cavity of diameter $\phi_2$, this first cavity extending along a main axis and being adapted to receive a wick that is capable of soaking the end piece with a combustible composition, and
an upper part having a peripheral side wall comprising an inner face of essentially frustoconical shape delimiting a second cavity of depth P, an outer face, an upper face of circular shape and a base, the inner face having a lower end of diameter $\phi_3$ greater than $\phi_2$ and an upper end of diameter $\phi_4$ greater than $\phi_3$, the upper end of the side wall communicating with the atmosphere and the base communicating with the first cavity,
at least a part of the outer face of the peripheral side wall is doped with a catalyst,
a sleeve arranged in the extension of the lower part of the end piece and delimiting a third cavity extending the first cavity of the lower part, and
an insert arranged in the first cavity of the end piece and having a surface in contact with the base of the end piece,
the porous material is obtained from a composition comprising, as a percentage of the total weight of this composition, between 0 and 5% of at least one heat-conducting compound, with a thermal conductivity of greater than 60 watts per meter-kelvin, between 30% and 70% of at least one refractory compound, between 2% and 30% of at least one binder, and between 5% and 40% of at least one pore-forming agent, and
in that all of the circular-shaped upper face is also doped with the catalyst.

The catalyst used in the context of embodiments of the present invention may be, for example, a catalyst based on a metal belonging to groups 9 or 10 of the Periodic Table of the Elements (according to the terminology recommended by the IUPAC).

The insert may be made of the same porous material as the burner. It may also be made of another porous material.

With such a composition, the porous material of the burner according to an embodiment of the invention has a porosity of between 57% and 63%, and preferably of about 59%, and interconnections of between 8 and 11 μm.

For the purposes of embodiments of the present invention, the term "interconnections" means the median diameter of the porous interconnections.

Advantageously, at least a part of the inner face of the peripheral side wall may also be doped with the catalyst. This makes it possible to further improve the operating performance in the presence of an air conditioner or ventilation, as shown in the examples hereinbelow.

Advantageously, the depth P of the second cavity may be between 2 and 8 mm, preferably between 6 and 7.5 mm and better still about 7 mm.

Advantageously, the lower end of the inner face may be terminated with a counterbore of diameter $\phi_3$, communicating with the first cavity.

For the purposes of embodiments of the present invention, the term "counterbore" means cylindrical machining made around a piercing communicating with the first cavity of the lower part of the end piece.

By virtue of the presence of the counterbore and also of the nature and porosity of the porous material of which the burner is made, the operating performance in the presence of air conditioning is further improved.

Advantageously, the outside diameter $\phi_1$ of the lower part of the end piece may be between 14 and 17 mm, preferably between 15 and 16 mm and better still about 15.6 mm.

Advantageously, the porous material is obtained from a composition comprising, as a percentage of the total weight of the composition, between 0.5% and 2% of the heat-conducting compound, between 40% and 70% of the refractory compound, between 5% and 25% of the binder, and between 8% and 35% of at least one pore-forming agent.

The composition of the porous material according to embodiments of the invention especially comprises heat-conducting compound and a refractory compound.

As heat-conducting compound that may be used in the porous material of the burner according to embodiments of the invention, use may advantageously be made of silicon carbide, preferably present in a proportion of 1% by weight relative to the total weight of the composition. The percentage of heat-conducting compound (between 0 and 5%, and preferably about 1%) is optimized so as to obtain ideal operating characteristics.

As refractory compound, use will preferably be made of a refractory compound with a thermal conductivity below the thermal conductivity of the heat conductor. Advantageously, the refractory compound may be chosen from the group constituted by alumina, silica, mullite, zirconia and cordierite, and mixtures thereof. The refractory material is preferably mullite. The mullite may, for example, be replaced or mixed with alumina, silica, zirconia, cordierite, or a mixture thereof. Silica is preferably introduced into the composition of the invention as a mixture with another refractory compound. In addition to its good mechanical behaviour at high temperature, the refractory compound plays a main role as insulator in the porous material obtained from the composition according to the invention.

Besides the heat-conducting compound and the refractory compound, the composition of the porous material according to embodiments of the invention comprises a binder and a pore-forming agent.

The term "binder" means a mineral compound which allows sintering at a temperature of less than or equal to 1100° C.

The binder is advantageously a glass with a variable percentage of silica, more particularly an oxide-based plain glass, for example including about 70% of silica and about 30% of calcium and sodium oxides, or a special glass including oxides of various elements such as boron or phosphate, for example a borosilicate glass.

The binder improves the formability, gives the raw mechanical cohesion of a piece and makes it possible to obtain a porous and mechanically strong material. The binder is chosen in particular from low-temperature-sintering compounds, i.e. compounds that allow sintering of the composition in which they are included at this temperature, of less than or equal to 1100° C. For example, during the temperature rise during sintering of the composition of the invention, the glass softens and wets the particles of heat-conducting compound. A vitreous phase is thus obtained. Next, during the temperature fall, the particles are bonded together during the solidification of the vitreous phase.

As pore-forming agent that may be used in the porous material of the burner according to embodiments of the invention, any pore-forming compound (natural or synthetic) whose particle size is governed and controlled, especially during its manufacture and its storage, may advantageously be chosen. For example, polymethyl methacrylate (PMMA) may advantageously be used as pore-forming agent. This agent may advantageously be present in a proportion of from 18% to 30% by weight relative to the total weight of the composition. The pore-forming agent allows the formation of pores during the sintering of the composition according to embodiments of the invention.

Thus, preferentially, the porous material may be made from a composition of the order of 1% of silicon carbide, between 60% and 70% of mullite, between 5% and 15% of glass, and about 18% to 30% of PMMA.

With such a composition, the porous material of the burner according to the invention has a porosity of about 60%, and interconnections of about 9.5 μm.

Advantageously, the sleeve of the burner may have a length of between 10 and 20 mm, and preferably about 14 mm. As illustrated in the examples, it is possible to achieve good performance qualities in terms of resistance to air conditioning with a burner according to embodiments of the invention having a sleeve length that may be as short as 12 mm.

A subject of the present invention is also a catalytic combustion bottle, which is suitable for containing a combustible liquid and for receiving on its neck a catalytic combustion burner receiving a wick which is soaking in the liquid, the bottle is equipped with a burner according to an embodiment of the invention as defined previously.

Other characteristics and advantages of the invention will emerge clearly from the detailed description that is made thereof hereinbelow, as a guide and with no limitation whatsoever, with reference to the attached drawings.

BRIEF DESCRIPTION OF THE DRAWINGS

The technical characteristics common to these two figures are each designated by the same reference numeral in the figures concerned.

DETAILED DESCRIPTION OF THE DRAWINGS

Figure 1:
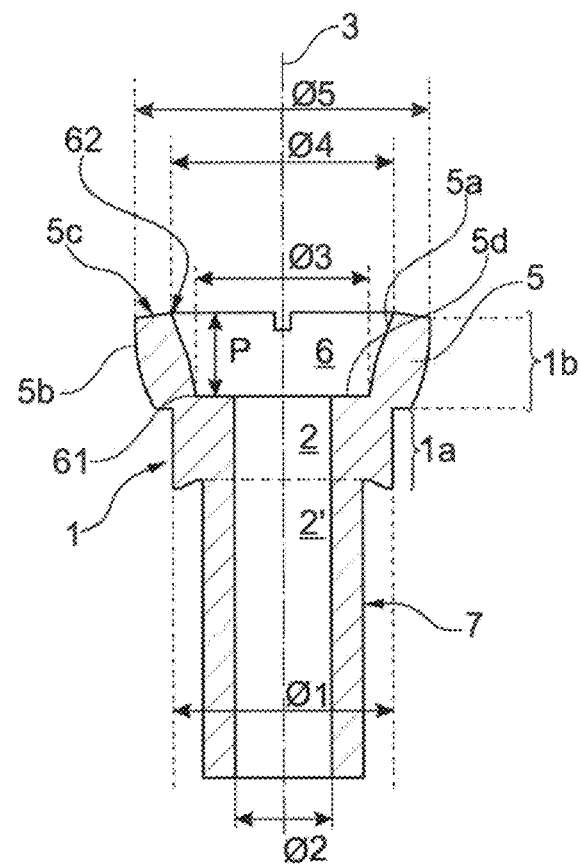
FIG. 1 represents schematically a cross section of a first example of a burner that may be used in the context of an embodiment of the present invention.
Figure 5:
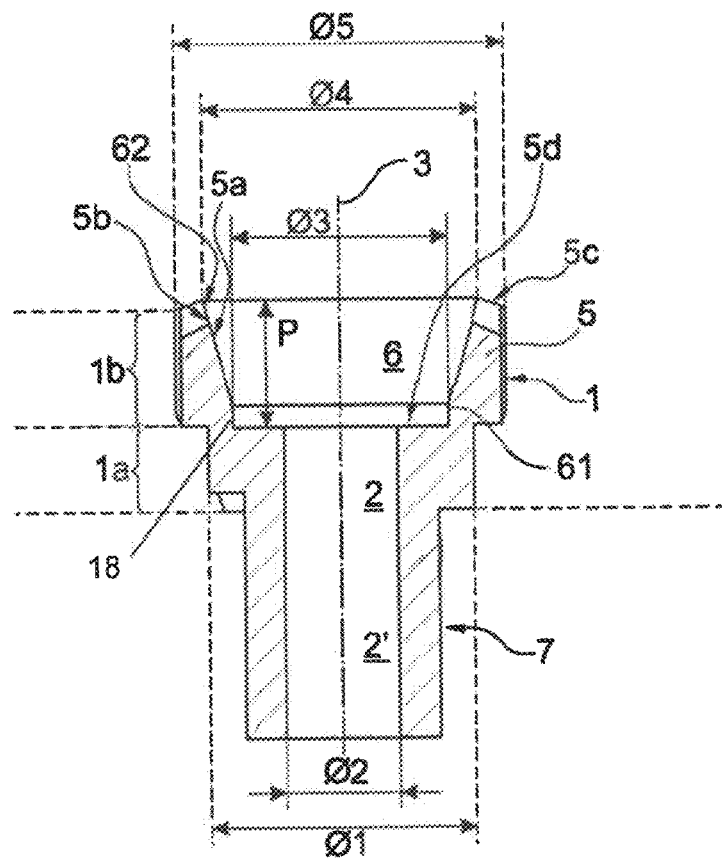
FIG. 5 represents schematically a cross section of a second example of a burner that may be used in the context of the present invention.
Figure 6:
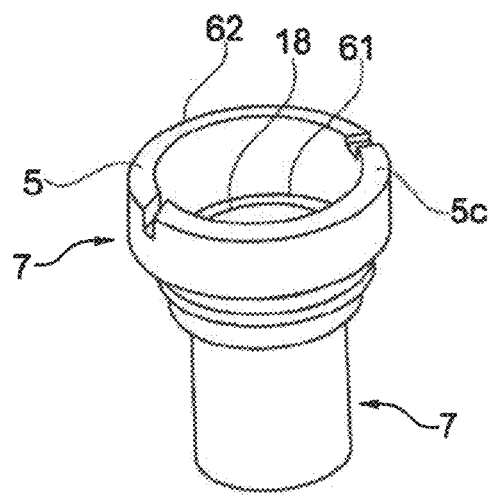
FIG. 6 is a perspective view of the burner illustrated in FIG. 5.

FIGS. 1, 5 and 6 show two examples of burners 10 that may be used in the context of the present invention. These two examples of burner 10 each comprise, on the one hand, an end piece 1 with a lower part 1a and an upper part 1b, and, on the other hand, a sleeve 7 arranged in the extension of the lower part 1a of the end piece 1.

As more particularly regards the end piece 1, it comprises:

the lower part 1a of outside diameter $\phi_1$ and delimiting a first cavity 2 of diameter $\phi_2$, this first cavity 2, which extends along a main axis 3, being adapted to receive a wick that is capable of soaking the end piece 1 with a combustible composition, and an upper part 1b having a peripheral side wall 5 comprising an inner face of essentially frustoconical shape and delimiting a second cavity 6 of depth P, an outer face of essentially cylindrical shape (but frustoconical at its base) and of diameter $\phi_5$, an upper face and a base communicating with the first cavity.

The inner face has a lower end 61 of diameter $\phi_3$ greater than $\phi_2$ and an upper end 62 of diameter $\phi_4$ greater than $\phi_3$, the upper end 62 of the side wall communicating with the atmosphere and the lower end 61 being connected to the base 5d. The first 2 and second 6 cavities communicate together.

As more particularly regards the sleeve (also known as the barrel) 7, it is arranged in the extension of the lower part 1a of the end piece 1. It delimits a third cavity 2' extending the first cavity 2 of the lower part. This sleeve is constituted of the same porous material as the end piece.

FIGS. 5 and 6 schematically show, respectively, a schematic cross section and a view in perspective of a second burner example, which differs from the first burner example in that, in the second burner example, the lower end 61 of the inner face terminates with a counterbore 18 of diameter $\phi_3$, communicating with the cavity 2. In the first burner example represented in FIG. 1 (without counterbore), the inner face is entirely frustoconical between its two ends 61 and 62.

The two burner examples (represented in FIGS. 1, 5 and 6) each comprise an insert 8 arranged in the second cavity 6 of the end piece 1 and having a surface 8a in contact with the base of the end piece.

In addition, at least a part of their outer face is doped with a catalyst, for example based on a metal belonging to groups 9 or 10 of the Periodic Table of the Elements (according to the terminology recommended by the IUPAC).

When the first burner example does not comprise any catalyst on its face, it is used as control in the tests of behavior with respect to air conditioning (designated hereinbelow by the reference 1C).

When the first burner example does not comprise any catalyst doping its face, it is used as first burner example according to an embodiment of the invention in the tests of behavior with respect to air conditioning (designated hereinbelow by the reference 1).

The second burner example comprises a catalyst doping its face, and is used as second burner example according to an embodiment of the invention in the tests of behavior with respect to air conditioning (designated hereinbelow by the reference 2).

Figure 2:
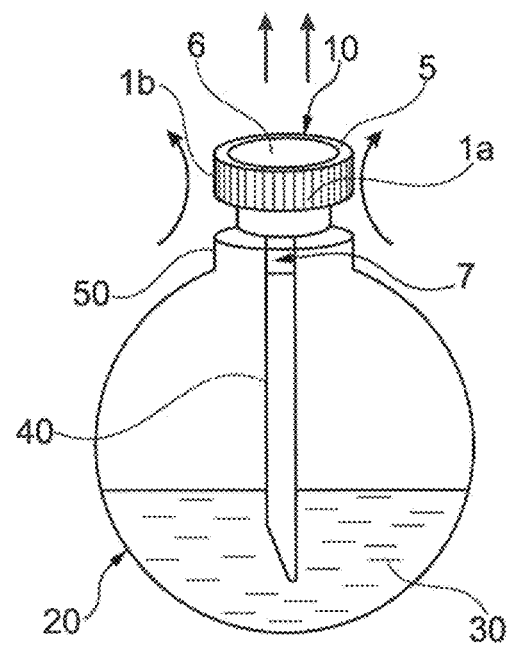
FIG. 2 is a schematic front view of a bottle equipped with one of the combustion burners represented in FIG. 1, on the one hand, and in FIGS. 5 and 6, on the other hand.

In order to test the catalytic functioning in the presence of air conditioning of the burners represented in FIGS. 1, 5 and 6, these burners were placed in a catalytic combustion bottle 20, represented in FIG. 2.

Figure 3:
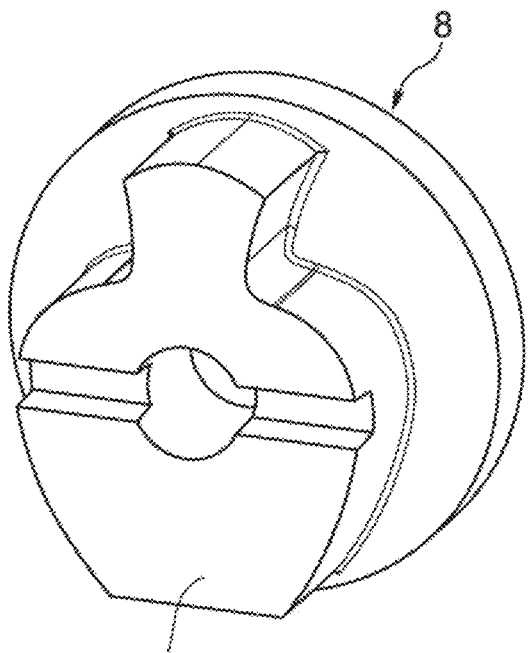
FIGS. 3 and 4 represent, respectively, a view in side perspective and a top view of an insert that may be used in the burner according to an embodiment of the invention.

Such a bottle 20 contains during functioning a combustible liquid 30. The burner 10 (either the burner according to an embodiment of the invention as represented in FIG. 5, or the prior art burner represented in FIG. 1, each equipped with an insert as represented in FIG. 3) is installed in the neck 50 of the bottle (for example with the aid of a metallic seat placed in the neck 50). A wick 40 is received inside the cavities 2 and 2' of the burner 10, this catalytic combustion wick 40 receiving a wick (40) which is soaking in the liquid 30. The bottle 20 may be a bottle of any shape having a neck 50 into which is fitted the burner 10. The combustible liquid 30 is usually an alcohol, for example isopropyl alcohol, or any other suitable combustible liquid that is compatible with the legislation in force in this field. In particular, this combustible must be such that its vaporization and its catalytic combustion do not give off any unpleasant odor. The combustible liquid 30 may also comprise a fragranced material and/or an active material. The wick 40 is any known wick, for example a wick made of cotton, or a wick made of mineral material, for example made of mineral fibers.

During functioning, the combustible liquid 30 in the bottle 20 rises in the wick 40 by capillary action and penetrates the pores of the porous material of the burner, which, when it has been preheated, ensures its catalytic combustion.

The examples that follow illustrate embodiments of the invention, in connection with the figures, without, however, limiting the scope thereof In these examples, unless otherwise indicated, all the percentages and parts are expressed as mass percentages.

EXAMPLES

Compounds Included in the Composition of the Porous Materials Used:
   heat-conducting compound: silicon carbide,
   refractory compound: mullite,
   binder: glass,
   pore-forming agent: polymethyl methacrylate (PMMA).
Compositions of the Porous Material:
   The burners used in the examples are made by dry pressing from compositions C1 and C2 below indicated in Table 1. For each of these compositions, the porosity of the ceramic structure and the median diameter of the interconnections have been indicated in Table 1.

TABLE 1

| Composition | Mullite (%) | SiC (%) | Glass (%) | PMMA (%) | Porosity (%) | Interconnection diameter (μm) |
|---|---|---|---|---|---|---|
| C1 | 64 | 5 | 10 | 21 | 58% to 60% at 975° C. | 9 |
| C2 | 66.5 | 1 | 11.5 | 21 | 60.2% at 1050° C. | 9.5 |
| C3 | 67 | 0.5 | 11.5 | 21 | 58.9 | — |

Figure 4:
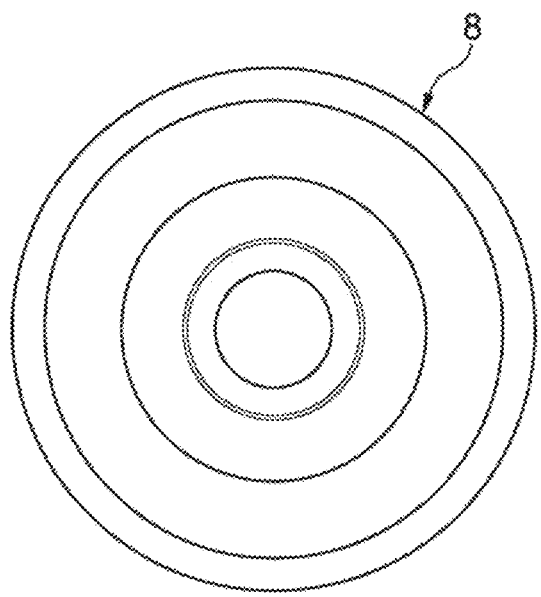

Catalysts
   The catalyst used (whether on parts 5a, 5b or 5c of the burner) is a metal belonging to groups 9 or 10 of the Periodic Table of the Elements.
Burners Used:
As Comparative Example:
   Burner 1C (represented in FIG. 1), the outer face of which is doped with a catalyst impregnating it, the burner 1C being constituted of a porous material obtained from composition C1.
As Examples According to Embodiments of the Invention:
   burner 1 (also represented in FIG. 1 and comprising the insert represented in FIGS. 3 and 4) identical to burner 1C, except for its face which is doped with the same catalyst as that of the outer face, burner 1 also being constituted of a porous material obtained from composition C1.
   burner 2 (represented in FIGS. 5 and 6 and comprising the insert represented in FIGS. 3 and 4), the outer face and the upper face of which are doped with the same catalyst which impregnates them, burner 2 being constituted of a porous material obtained from composition C2.
   burner 3 (represented in FIGS. 5 and 6 and comprising the insert represented in FIGS. 3 and 4), the outer face and the upper face of which are doped with the same catalyst which impregnates them, burner 3 being constituted of a porous material obtained from composition C3.

During functioning, when the burner is equipped with a catalyst in its circular peripheral part, the part of the combustible liquid which reaches this part undergoes catalytic combustion thereat, which keeps this part at a high temperature.

Bottle used: the one shown in FIG. 2 for burners 1C, 1 and 2.

Wick used: cotton wick (for burner 3, two different wicks were tested).

Combustible liquid used: isopropyl alcohol.

Tests and Measurements

1) Porosity (%) and Diameter D of the Interconnections

The open porosity of the porous material constituting the burner is measured by mercury intrusion into the material of a Micromeritics Autopore IV 9510 brand porosimeter. This measurement is taken at a maximum pressure of 414 MPa approximately, which corresponds to a minimum detectable pore size of about 0.0035 μm.

Method and Operating Protocol:

The measurement of the porosity by mercury intrusion is based on the principle of penetration of an unreactive liquid into a porous material, by immersing the material in the liquid and increasing the pressure isostatically. Mercury, which does not react with the majority of materials, is furthermore an ideal liquid due to the high value of its contact angle, it does not wet the majority of materials.

From this measurement, the pore size is determined in terms of the diameter D in μm (interconnection diameter), then penetrated, which is inversely proportional to the applied pressure, P, according to an embodiment of the Washburn equation:

$$D = \frac{-4\gamma\cos\Theta}{P}$$

with: γ: surface tension of mercury,
γ=0.00485 N/cm (485 dynes/cm).
θ: contact angle of mercury, θ=140°

Figure 19:
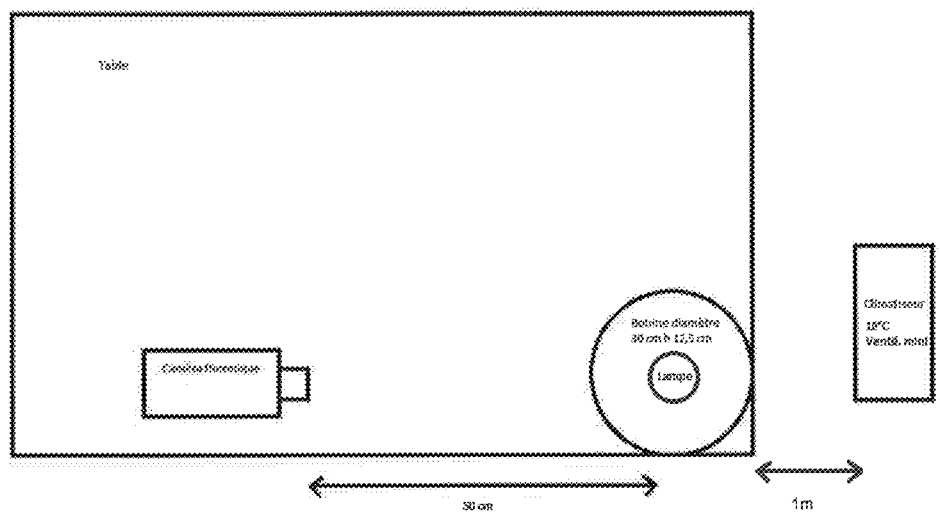
FIG. 19 illustrates the protocol for measuring by infrared camera the impact of air conditioning on the temperature of the burner during functioning.

2) Operating Characteristics of the Burners 10 Installed on the Bottle 20 in the Presence of an Air Conditioner at 18° C. With Ventilation The test protocol is represented in FIG. 19. It consists globally in measuring, by infrared (IR) thermograph using an IR thermal camera, the temperature on each of the burners tested, placed at a reasonable distance from an air conditioner (the power of which is 800 W in the context of the tests performed). These measurements are compared, for each burner tested (control 1C and according to embodiments of the invention 1 and 2), with measurements taken without ventilation.

Figure 7:
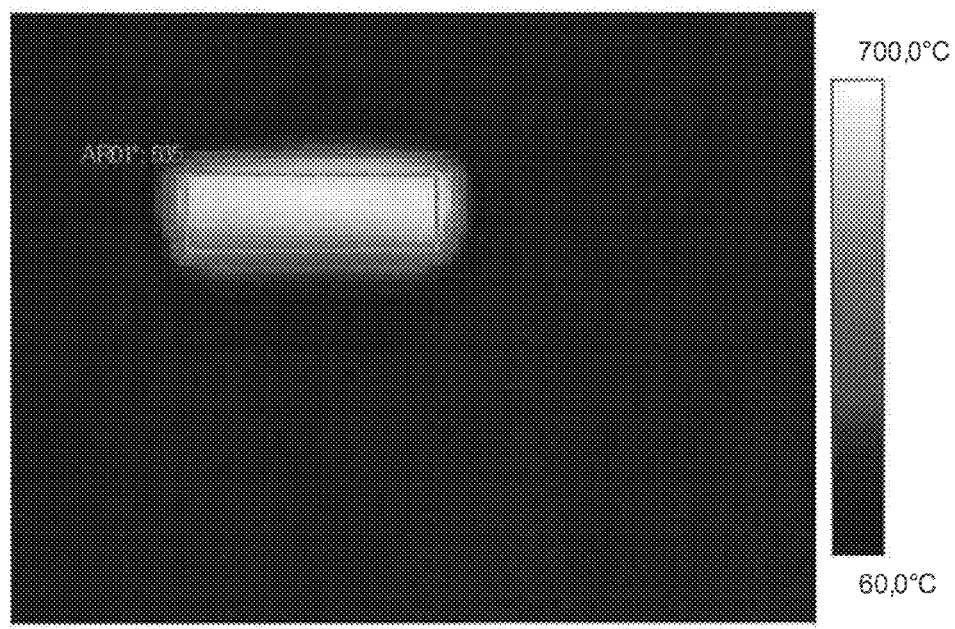
FIGS. 7 to 18 are IR thermographs produced to show the impact of air conditioning on a burner according to an embodiment of the invention, on the one hand, and on a control burner not having any catalyst on the circular zone.
Figure 8:
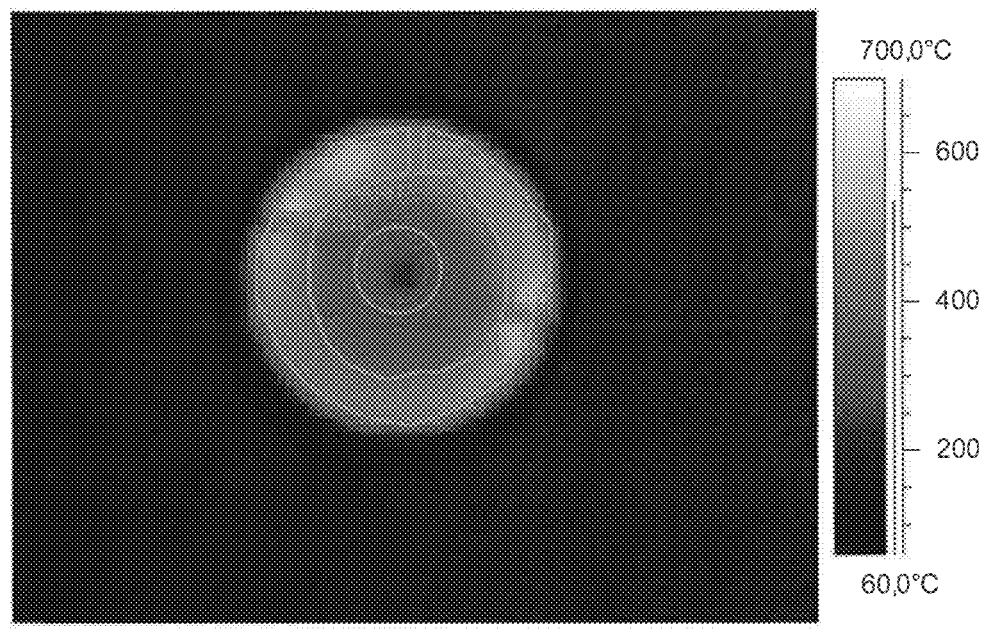
Figure 9:
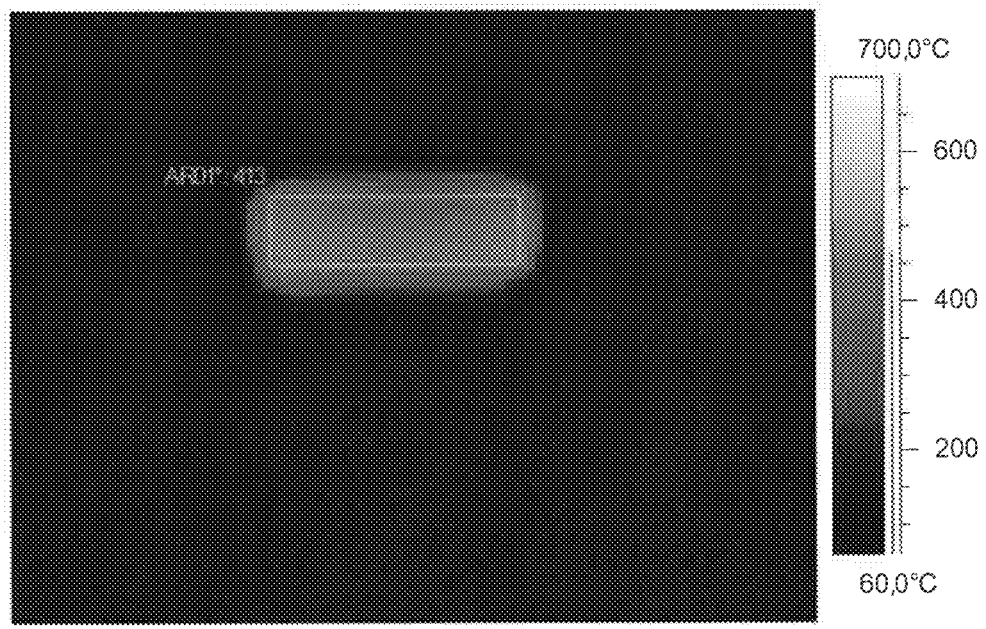
Figure 11:
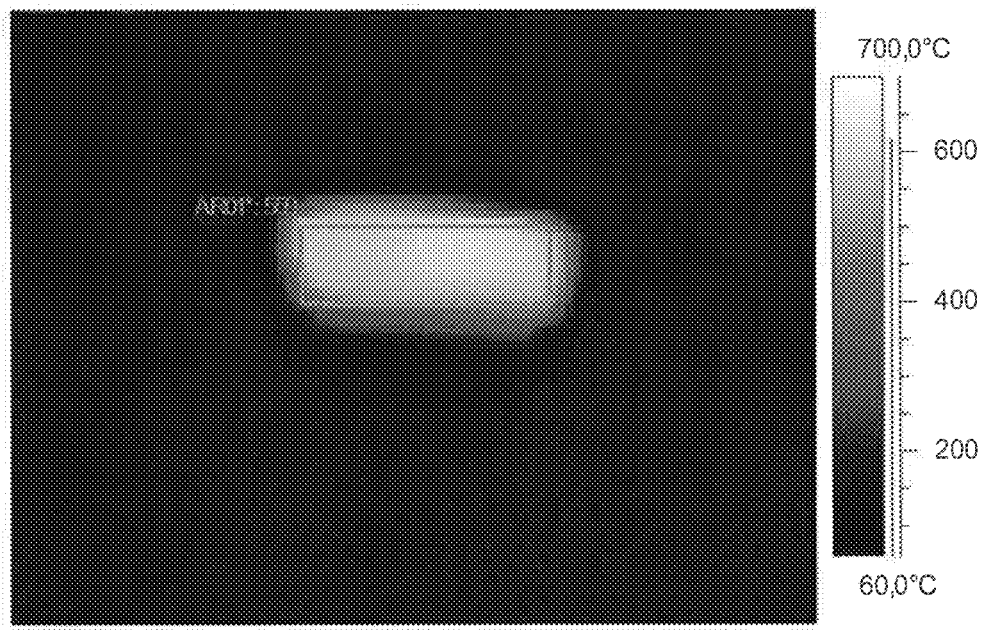
Figure 12:
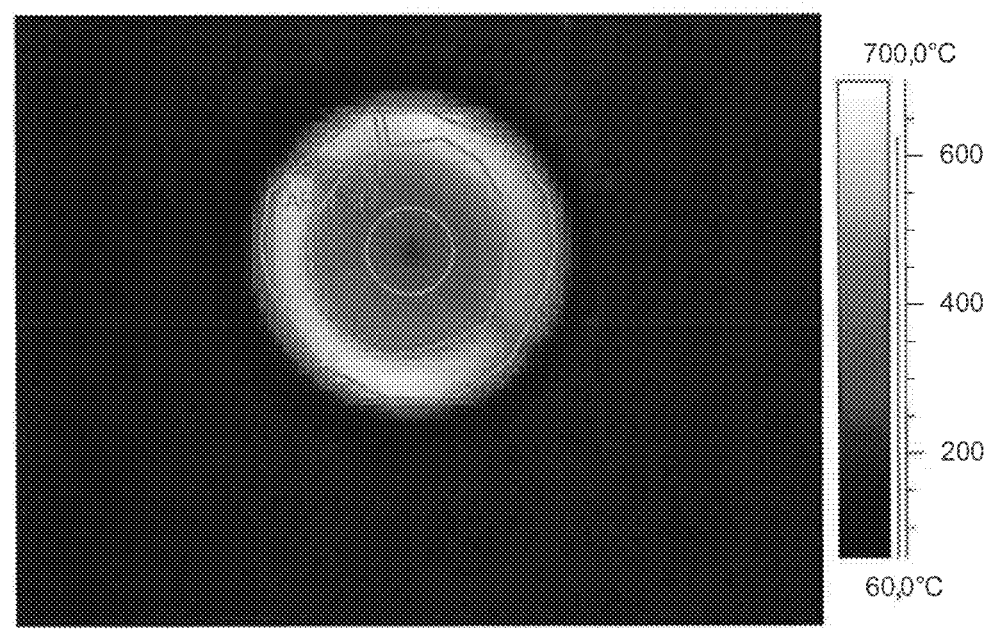
Figure 13:
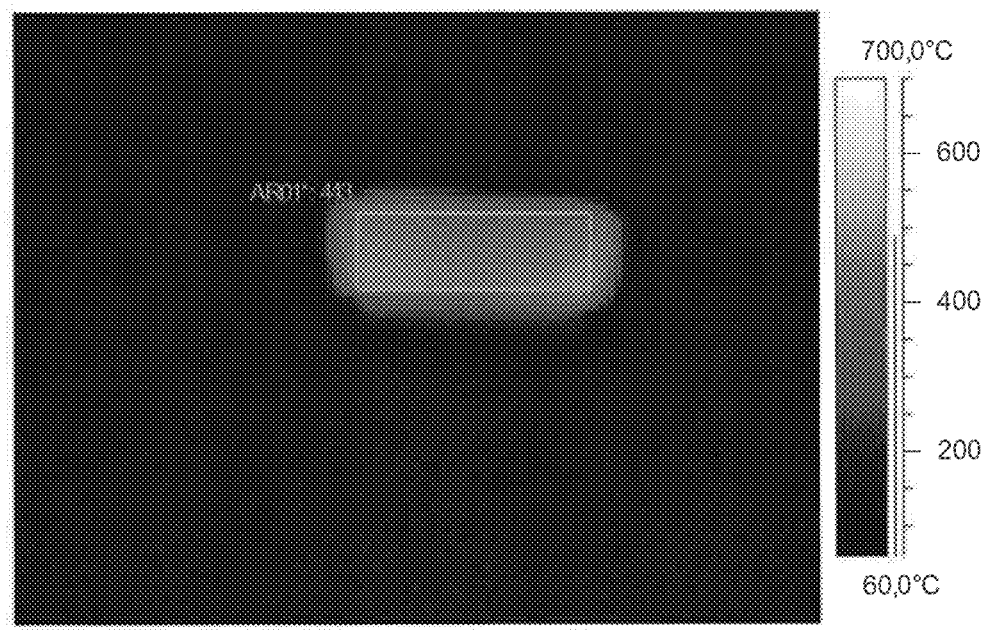
Figure 15:
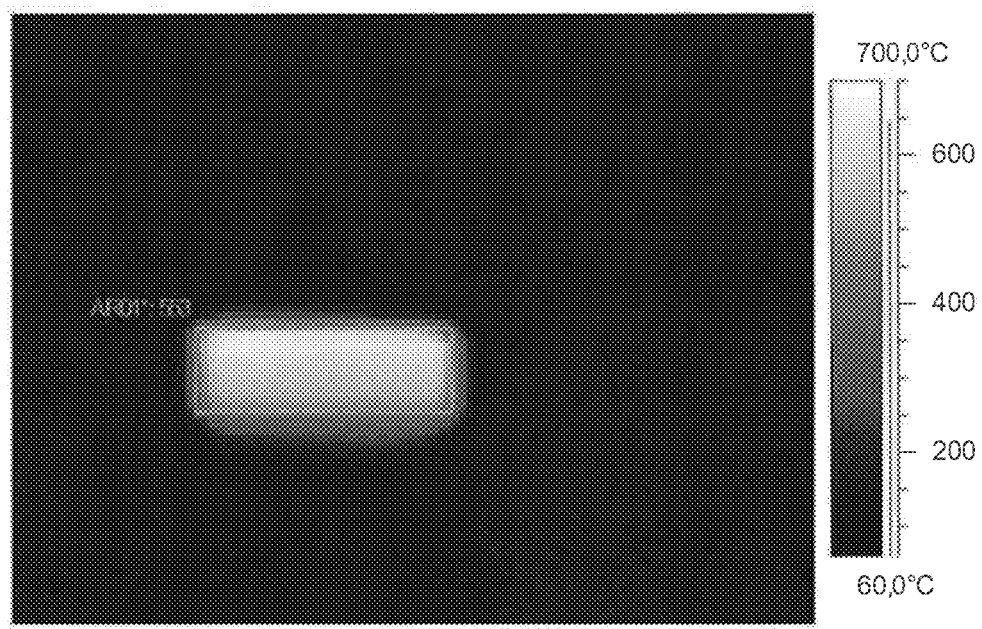
Figure 16:
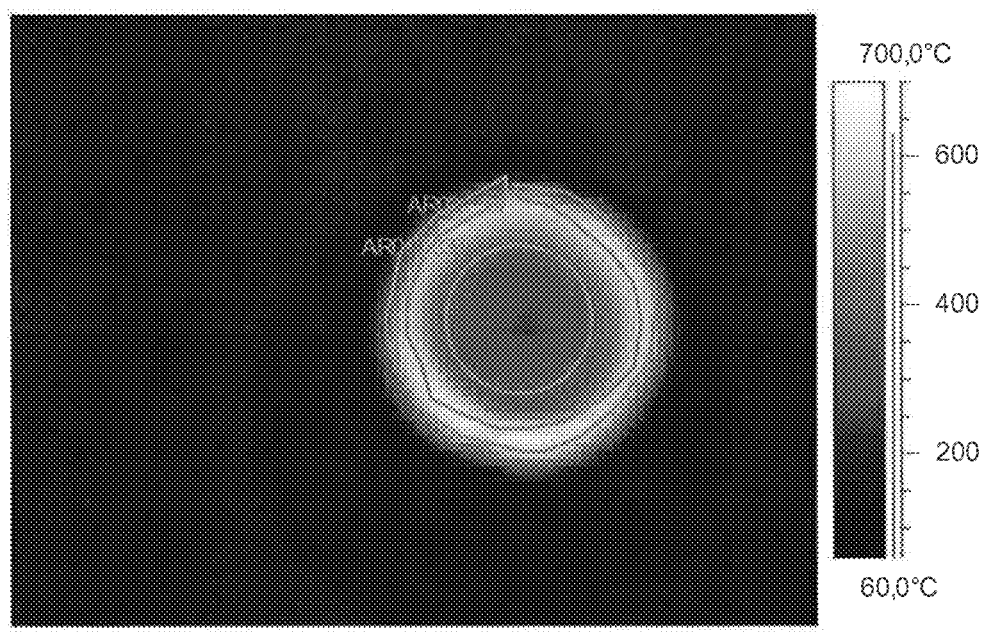
Figure 17:
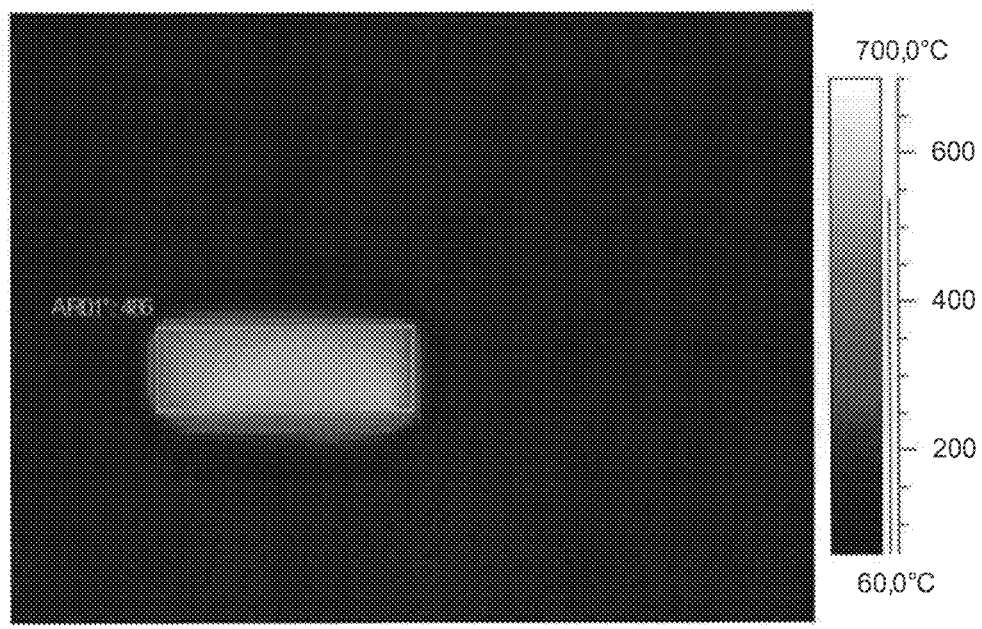

The thermographs produced are detailed below:

Burner 1C:
  without air conditioning: FIGS. 7 and 8;
  with air conditioning: FIG. 9 (measurement taken on the side opposite the air conditioning) and FIG. 10 (measurement taken on the side facing the air conditioning);

Burner 1:
  without air conditioning: FIGS. 11 and 12;
  with air conditioning: FIG. 13 (measurement taken on the side opposite the air conditioning) and FIG. 14 (measurement taken on the side facing the air conditioning);

Burner 2:
  without air conditioning: FIGS. 15 and 16;
  with air conditioning: FIG. 17 (measurement taken on the side opposite the air conditioning) and FIG. 18 (measurement taken on the side facing the air conditioning).

When the measurement is taken on the side of the burner that is opposite the flow of air coming from the air conditioner, the air flow has little impact on the temperature measured on this side of the burner, as shown by comparison of FIGS. 7 and 9 (burner 1C), FIGS. 11 and 13 (burner 1 according to an embodiment of the invention), and FIGS. 15 and 17 (burner 1 according to an embodiment of the invention). This temperature decreases very little for burners 1 and 2 according to an embodiment of the invention, and slightly more for the control burner 1.

Figure 10:
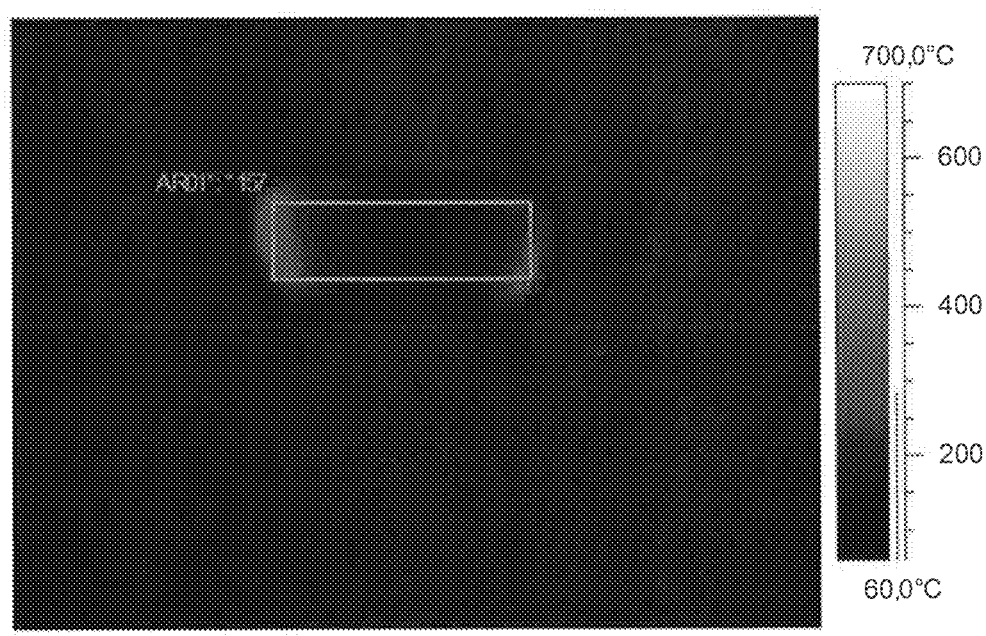
Figure 14:
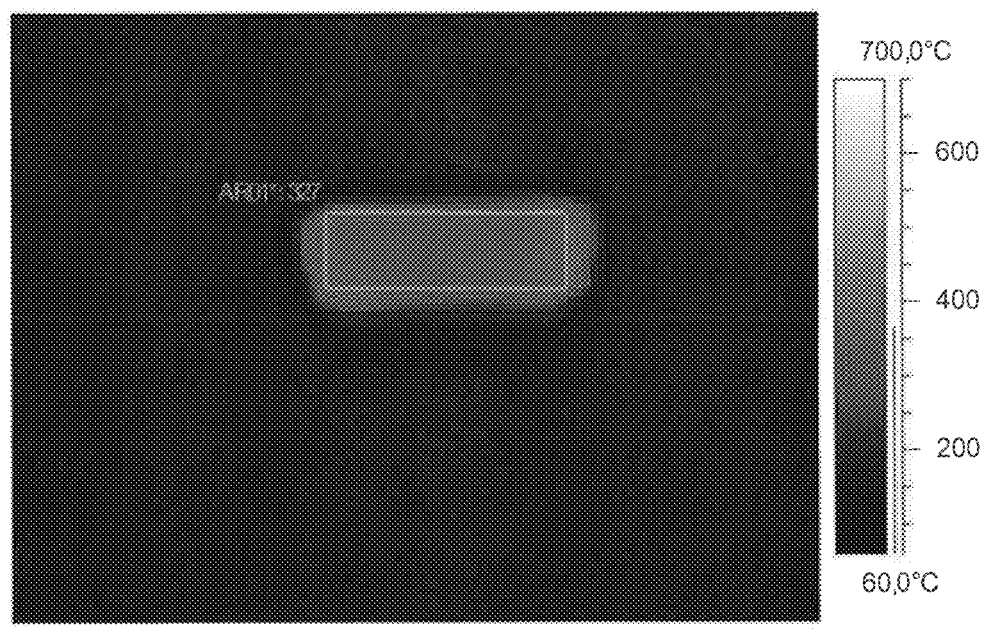
Figure 18:
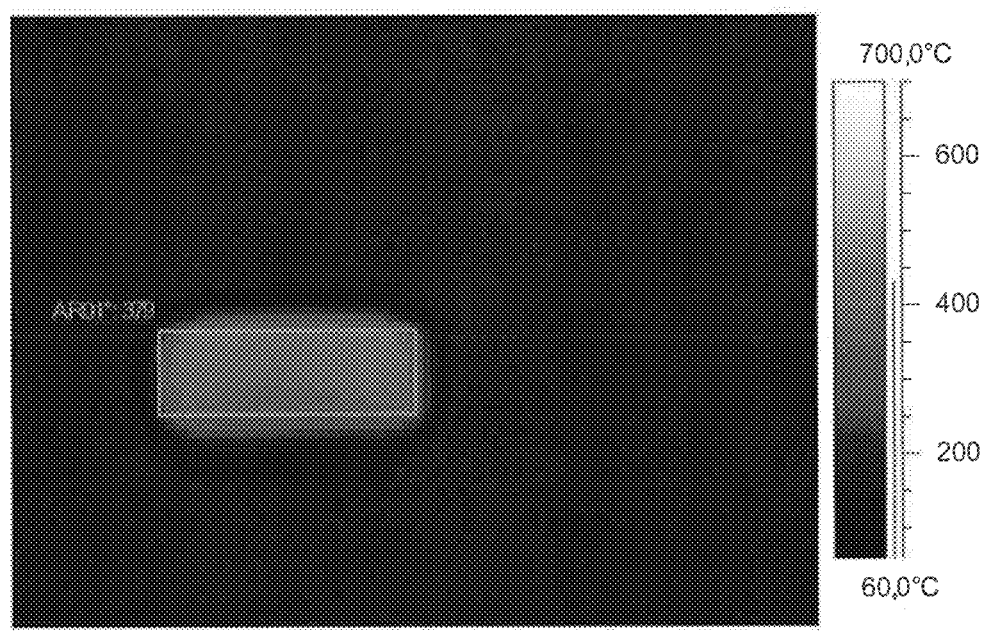

This is not likewise the case when the measurement is taken on the side of the burner facing the air conditioner: burners 1 and 2 according to an embodiment of the invention show better resistance than the control burner 1C, as shown by comparison of FIGS. 7 and 10 (drastic drop for the control burner), that of FIGS. 11 and 14, and finally that of FIGS. 15 and 18. It is considered that when the temperature measured at a given place on the catalyst is below 300° C., the catalyst has a high likelihood of extinguishing rapidly.

The temperatures measured are collated in Table 2 below:

TABLE 2

| | Temperature measurement without air conditioning | | | Temperature measurement with air conditioner | |
|---|---|---|---|---|---|
| | Side Face 5b | Top Face 5c | Centre | Side opposite the air conditioner | Side facing the air conditioner |
| Burner 1 C. | 535° C. | 460° C. | 283° C. | 413° C. | 157° C. |
| Burner 1 | 559° C. | 521° C. | 313° C. | 443° C. | 327° C. |
| Burner 2 | 553° C. | 537° C. | 339° C. | 486° C. | 379° C. |
| Burner 3 (test wick 1) | 546° C. | 559° C. | 347° C. | 483° C. | 404° C. |
| Burner 3 (test wick 2) | 556° C. | 532° C. | 336° C. | 523° C. | 411° C. |

These tests show that the presence of a catalyst on the circular zone of the burner makes it possible to maintain the temperature of the burner when it is subjected to a strong air current such as, for example, that emitted by a portable air conditioner, both for an SiC content of 1% and for an SiC content of 0.5%. This catalyst allows thermal conduction of the heat to the burner zone, which, when subjected to an air current, does not ultimately become unprimed.

The invention claimed is:

1. Catalytic combustion burner made of porous material, comprising:
   an end piece comprising:
      a lower part of outside diameter $\phi_1$ and delimiting a first cavity of diameter $\phi_2$, said first cavity extending along a main axis and being adapted to receive a wick that is capable of soaking the end piece with a combustible composition, and
      an upper part having a peripheral side wall comprising an inner face of essentially frustoconical shape and delimiting a second cavity of depth P, an outer face, an upper face of circular shape and a base, said inner face having a lower end of diameter $\phi_3$ greater than $\phi_2$ and an upper end of diameter $\phi_4$ greater than $\phi_3$, the upper end of said side wall communicating with the atmosphere and said lower end of said base communicating with said first cavity, the lower end of said inner face terminating with structure defining a counterbore of diameter $\phi_3$, communicating with said second cavity, the lower end of said inner face terminating with structure defining a counterbore of diameter $\phi_3$, communicating with said second cavity, at least a part of said outer face of said peripheral side wall is doped with a catalyst, a sleeve arranged in the extension of said lower part of the end piece and delimiting a third cavity extending said first cavity of said lower part, and an insert arranged in said second cavity of the end piece and having a surface in contact with said base of the end piece, wherein said porous material is obtained from a composition comprising, as a percentage of the total weight of said composition, between 0.5 and 1% of silicon carbide as a heat-conducting compound, between 30% and 70% of at least one refractory compound, between 2% and 30% of at least one binder, and between 5% and 40% of at least one pore-forming agent, and in that all of said circular-shaped upper face is doped with said catalyst.

2. Burner according to claim 1, in which at least a part of said inner face of said peripheral side wall is doped with said catalyst.

3. Burner according to claim 1, in which the depth P of said second cavity is between 2 and 8 mm.

4. Burner according to claim 3, in which the depth P of said second cavity is between 6 and 7.5 mm.

5. Burner according to claim 4, in which the depth P of said second cavity is 7 mm.

6. Burner according to claim 1, in which each said refractory compound is chosen from the group constituted of alumina, silica, mullite, zirconia and cordierite, and mixtures thereof.

7. Burner according to claim 1, in which said binder is a mineral compound which allows sintering at a temperature of less than or equal to 1100° C.

8. Burner according to claim 7, in which said mineral compound is a glass.

9. Burner according to claim 8, in which said glass is a borosilicate glass.

10. Burner according to claim 1, in which the pore-forming agent is polymethyl methacrylate (PMMA), which is present in a proportion of from 18% to 30% by weight relative to the total weight of said composition.

11. Burner according to claim 1, according to which said porous material is obtained from a composition comprising, as a percentage of the total weight of said composition, about 1% of silicon carbide, between 60% and 70% of mullite, between 5% and 15% of glass, and between 18% and 30% of PMMA.

12. Burner according to claim 11, in which said sleeve has a length of between 10 and 20 mm.

13. Burner according to claim 12, in which said sleeve has a length of 14 mm.

14. Catalytic combustion bottle, which is suitable for containing a combustible liquid and for receiving on its neck a catalytic combustion burner receiving a wick which is soaking in said liquid, wherein said bottle is equipped with a burner as defined according to claim 1.

* * * * *